United States Patent [19]

Madoian et al.

[11] 4,195,529

[45] Apr. 1, 1980

[54] DEVICE FOR MOVING THE PICKUPS OF A FLAW DETECTION SYSTEM THROUGH A PIPELINE

[76] Inventors: Ashot A. Madoian, prospekt Pobedy, 16, kv. 28; Viktor G. Kantsedalov, prospekt Pobedy, 103, kv. 95; Petr B. Samoilenko; Valentin P. Samoilenko, both of ulitsa Vl. Shevchenko, 29, kv. 19, all of Gorlovka Donetskoi oblasti, U.S.S.R.

[21] Appl. No.: 915,890

[22] Filed: Jun. 15, 1978

[30] Foreign Application Priority Data

Jun. 24, 1977 [SU] U.S.S.R. .............................. 2493651
Jun. 29, 1977 [SU] U.S.S.R. .......................... 2500413[I]

[51] Int. Cl.² ............................................. G01N 29/04
[52] U.S. Cl. .................................... 73/638; 324/220
[58] Field of Search ............... 73/432 R, 40.5 A, 592, 73/638; 324/219, 220, 221

[56] References Cited

U.S. PATENT DOCUMENTS

| | | | |
|---|---|---|---|
| 2,622,125 | 12/1952 | Bender | 324/220 |
| 3,439,527 | 4/1969 | Rohrer | 73/40.5 A |
| 3,754,275 | 8/1973 | Carter et al. | 324/220 X |
| 3,940,689 | 2/1976 | Johnson, Jr. | 324/221 |
| 4,052,887 | 10/1977 | Sheridan et al. | 73/592 |
| 4,063,157 | 12/1977 | Lorenzi | 324/220 X |
| 4,105,972 | 8/1978 | Smith | 73/638 |

*Primary Examiner*—Daniel M. Yasich
*Attorney, Agent, or Firm*—Fleit & Jacobson

[57] ABSTRACT

The disclosed device comprises two support end assemblies formed as cup-shaped sleeves adapted to be alternatingly engaged with the internal surface of a pipeline and interconnected by a motion member. The lateral surface of each sleeve defines and annular chamber with an elastic sheath thereby. The two sleeves are interconnected by a bellows fixed between the bottoms of the sleeves. The annular chambers and the bellows are connected to an air-compressor through an automatic control system arranged so that at the initial stage of a successive advancing step the leading chamber communicates with the ambient atmosphere, while the trailing chamber and the bellows are communicated to the pressure connection of the compressor, whereas at the final stage of the step the trailing chamber and the bellows are communicated with the suction connection of the compressor, while the leading chamber is under pressure.

7 Claims, 3 Drawing Figures

DEVICE FOR MOVING THE PICKUPS OF A FLAW DETECTION SYSTEM THROUGH A PIPELINE

The present invention relates to the art of inspecting the internal surface of pipelines and other fluid conduits for the presence of flaws therein, such as that using devices for non-destructive inspection of the condition of the structural material of the pipelines and conduits; and, more particularly, the present invention relates to devices for moving the pickups or transmitters of a flaw detection system through a pipeline.

The invention can be employed to utmost advantage for the inspection of the internal surface of lengthy pipelines, such as those incorporated in thermal power plants (TPP) and nuclear power plants (NPP), with their intricate three-dimensional paths and attitudes; particularly, in the areas presenting access problems, e.g. the increased-radiation reas of NPPs.

Furthermore, the invention can be utilized as effectively for the inspection of the internal surface of lengthy gas pipelines, oil pipelines, hot water supply networks including the underground ones.

The steady per-unit growth of the power ratings of thermal and nuclear power stations, the stepped-up initial parameters of their working fluid and the appearance on the power scene of turbine units of NPPs operating with wet steam—all these factors have applied a particular weight to the inspection of the condition of the metal in the major plant components, including the pipelines and other fluid conduits, both in the course of their delivery and erecting work, and during routine operation. This is directly linked with ensuring the dependability of the plant's performance, minimizing the downtime, providing for the personnel's safety and precluding environmental hazards.

It can be easily seen that this problem is best solved by providing devices enabling to conduct non-destructive remote inspection and monitoring, e.g. devices carrying flow-detection pickups or transmitters through the internal spaces of the plant and conduits.

There is already known a device for flaw detection from the internal space of pipelines and other fluid conduits, comprising a motion-providing member made up of annular brushes driven through successive reciprocations to move the device in the required direction.

A disadvantage of said known device is that it is incapable of dealing with pipelines having curving portions, same as portions of somewhat oval cross-section.

There is further known a device for carrying and moving the pickups of a flaw detection system, comprising two support end assemblies alternatingly engageable with the internal surface of the pipeline and interconnected by a motion member of which the length is variable upon one of the support end assemblies having engaged the surface of the pipeline (cf. SU Inventor's Certificate No. 473,447; IPG² G 01 N 27/00, published on Dec. 11, 1977). Each support end assembly comprises centering and retaining parts extending radially. In each support assembly there are three retaining parts spaced by 120° and three centering parts likewise spaced by 120°, the parts extending radially. The retaining parts are intended to arrest the device at the required spot of the pipeline and include each a support shoe mounted in a "floating" pivot of the plunger of a pneumatic cylinder operable to urge the shoe against the internal surface of the pipeline. The centering parts, in their turn, are intended to ensure that the device is centered, as it travels through the pipeline. Each centering part includes a guide roller adjoining the internal surface of the pipeline, mounted on the plunger rod of a pneumatic cylinder. Thus, every support end assembly of this device of the prior art comprises six pneumatic cylinders with their respective plunger rods, of which the axes extend radially within a single plane perpendicular to the axis of the pipeline, and are spaced by 60°. In other words, the two support end assemblies have as many as twelve such cylinders. In the device of the prior art the motion member interconnecting the two support end assemblies is in the form of a pneumatic cylinder having its axis aligned with the axis of the pipeline, the housing of the cylinder having secured thereto a sleeve for mounting the pickups as an assembly having its own pneumatic cylinder and electric actuator. The sequence of the operation of the pneumatic cylinders is such that at the initial stage of each successive step through the pipeline compressed air is first fed into the pneumatic cylinders of the centering parts, and then into the pneumatic cylinders of the retaining shoes, whereby the respective one of the support end assemblies is positioned and retained at the required spot within the pipeline. At this stage the pneumatic cylinders of the second support end assembly are deenergized, their spring-retracted plungers making the rollers and shoes clear the surface of the pipeline. Then compressed air is fed into the pneumatic cylinder of the motion member, whereby the plunger rod of this cylinder moves with the second-mentioned support end assembly, thus advancing the latter through the pipeline. Then compressed air is fed into the pneumatic cylinders of the second support end assembly to retain the latter in the pipeline, while the shoes and rollers of the first-mentioned support end assembly are retracted by the spring-retracted plunger rods to clear the surface of the pipeline, and this first-mentioned assembly is pulled toward the second-mentioned one. In this way the device is driven through a single step.

During each step the surface of the pipeline is inspected and monitored by the pickups mounted on the sleeve, the pickups being in any suitable assortment and arrangement.

A disadvantage of the device of the prior art is its complicated structure including as it does the great number of the pneumatic cylinders with their respective communication lines, which cannot but affect the reliability of the performance of the device and complicate its operation. Furthermore, the rigidity of the motion member would not ensure that it easily and dependably passes curvilinear portions of the pipeline, same as portions of an oval shape in cross-section, particularly, the areas of the pipeline having a varying curvature.

It is the main object of the present invention to provide a device for moving the pickups of a flaw detection system through a pipeline, which should be capable of passing through curvilinear portions of a pipeline.

It is another object of the present invention to provide the abovesaid device, which should be adequately dependable in operation.

It is still another object of the present invention to provide the abovesaid device, which should be simple to operate.

These and other objects are attained in a device for moving the pickups of a flaw detection system through a pipeline, including: a compressor; a pressure delivery connection of said compressor; an intake suction connection of said compressor; two support end assemblies adapted to alternatingly engage the internal surface of said pipeline, each said support end assembly having a cup-shaped sleeve with a lateral surface and a bottom and an elastic sheath accommodated on said lateral surface of said sleeve, defining therewith an annular chamber; a motion member having its length variable upon either one of said support end assemblies having engaged the surface of said pipeline, said motion member interconnecting said two support end assemblies and comprising a bellows secured between the respective bottoms of said two sleeves; an automatic control system; said chambers and said bellows communicating with said compressor via said automatic control system so arranged that at the initial stage of each successive step the leading, in the direction of the intended travel of the device, one of said chambers is connected to the atmosphere, while the other, trailing one of said chambers and said bellows are connected to the pressure delivery connection of said compressor, whereas at the final stage of the step said trailing chamber and said bellows are connected to said intake connection of said compressor, while said leading chamber is under pressure.

With the support end assemblies including the cup-shaped sleeves having each a chamber defined at its lateral surface by the elastic sheath, the device can be reliably retained at any required spot of the pipeline notwithstanding the latter's curvature, oval-shaped cross-section, surface flaws or the presence of smaller-diameter tap lines leading from the pipeline. Furthermore, with the motion member being in the form of the bellows secured between the bottoms of the cup-shaped sleeves, the device is capable of passing through portions of a pipeline, having any curvature that can be met in practical cases, owing to the flexibility of the bellows. The automatic control system is responsible for the preset sequence of connecting the respective chambers of the two support assemblies and the internal space of the bellows to the intake and pressure delivery connections of the compressor, so that the device advances through the pipeline.

It is expedient that the bellows should comprise a set of frustoconical elastic elements having each its opposite bases or ends secured to rigid rings adjoining the respective rings of the adjacent elements. The frustoconical elastic elements enable the bellows to acquire the three-dimensional positions required for its passage through curvilinear portions of the pipeline. The incorporation of the rigid rings between the elastic elements, on the other hand, precludes the variation of the flow passage area of the bellows when its internal space is connected to the suction source.

The automatic control system preferably includes a supply line connecting a two-way control valve with the trailing chamber and a control unit of this two-way valve, including a diaphragm-type actuator operatively connected to the two-way valve and communicating with the supply line through a pressure-controlled gate and a check valve arranged parallel with each other; a pressure-limiting means connecting the supply line with the internal space of the bellows, including a pressure-controlled gate and a check valve arranged parallel with each other; a pressure-controlled gate in the connection between the internal space of the bellows with the leading chamber; and a pressure-relief line including a diaphragm-type actuator and a valve for connection with the atmosphere, the last-mentioned line being also connected with the leading chamber. This preferred embodiment of the automatic control system enables to minimize the number of the connections and communications and to supply the device from a single compressor through the single two-way valve via the single supply line, which significantly enhances the reliability of the performance. The operation and maintenance of the device with its control system of this preferred type are simplified, since the adjustment of the system practically involves the more presetting of the three pressure-controlled gates to a required pressure values. The reduced number of the connections and communications brings down the weight of the auxiliary equipment advancing jointly with the device, which in its turn enables to increase both the payload of the device, e.g. to mount more pickups thereon, and its operating range.

The internal space of the bellows preferably accommodates therein an expansion-limiting means, e.g. including a length of a cable having its ends secured in the centres of the respective bottoms of the cut-shaped sleeves.

The expansion-limiting cable precludes damaging of the elements of the bellows, and while the device passes through a curvilinear portion of a pipeline, it becomes offset from the axis of the bellows and facilitates the curving of the path of the device. By providing for the permanent length of the advancing steps of the device, the expansion-limiting cable enables to locate the device in the pipeline.

The herein disclosed structure of the device offers fair conditions for accommodating therein flaw-detection pickups and transmitters. In a preferred embodiment of the invention the internal space of at least one of the two annular chambers accommodates pickups for acoustic or ultrasonic inspection of the pipeline, secured to the elastic sheath, while the internal space of at least one cut-shaped sleeve accommodates eddy-current pickups.

The invention will be further described in connection with a preferred embodiment thereof, with reference being had to the accompanying drawings, wherein.

Figure 1:
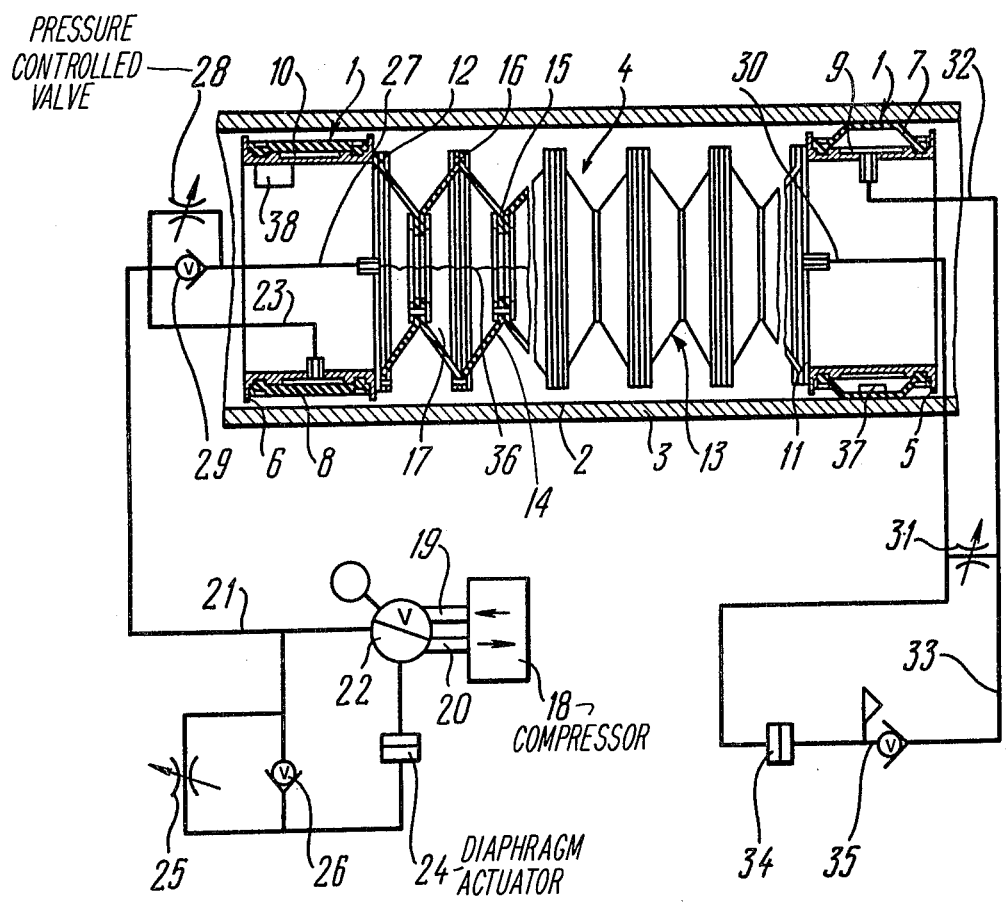
FIG. 1 shows schematically the general sectional view of a device for moving the pickups of a flaw detection system through a pipeline, jointly with the diagram of the automatic control system, in accordance with the invention, with the leading chamber being under pressure.
Figure 2:
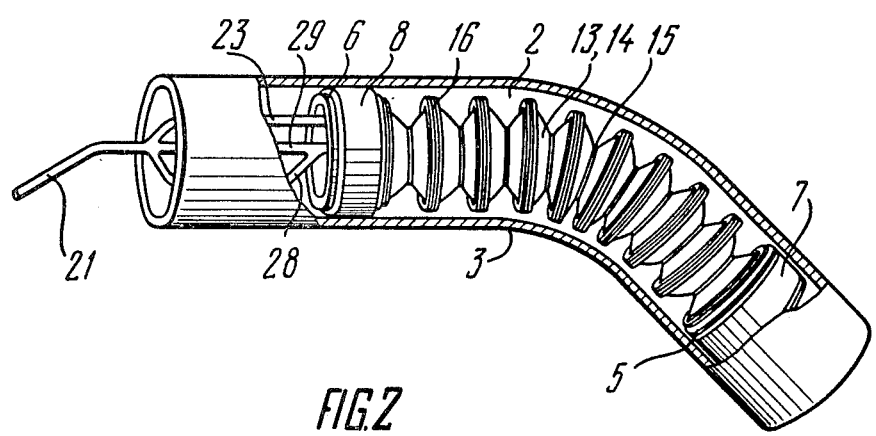
FIG. 2 illustrates the herein disclosed device passing through a curving portion of a pipeline.

Let us now consider FIG. 1 of the appended drawings, illustrating the device for moving the pickups of a flaw detection system through a pipeline. The pickups may be of the acoustic or ultrasonic type and of the eddy-current type, known and used per se for inspecting and monitoring the state of the surface of a pipeline. The device has two support end assemblies 1 alternatingly engageable with the internal surface 2 of the pipeline 3, interconnected by a motion member 4 of which the length is variable upon one of the support assemblies 1 having engaged the surface 2 of the pipeline 3. In accordance with the invention, the two support end assemblies 1 are in the form of respective cup-shaped sleeves 5 and 6 of which the lateral surfaces have mounted thereon elastic sheaths or bladders 7 and 8 defining with these respective lateral surfaces annular inflatable chambers 9 and 10. The two sleeves 5 and 6 have their respective bottoms 11 and 12 interconnected by a bellows 13 incorporated in the motion member 4 and including an array of frustoconical elastic elements 14, each element 14 having its opposite ends or bases secured to the respective rigid rings 15 and 16 adjoining the corresponding rings of the adjacent elements 14. The chambers 9 and 10 and the internal space 17 of the bellows 13 are connected to an air compressor 18 through an automatic control system. The automatic control system is so arranged that at the initial stage of each successive advancing step the chamber 9 which is the leading one in the required direction of the advance is connected to the ambient atmosphere; while the trailing chamber 10 and the internal space 17 of the bellows 13 are connected to the pressure delivery connection 19 of the compressor 18, whereas at the end of the step the trailing chamber 10 and the internal space 17 of the bellows 13 are connected to the intake connection 20 of the compressor 18, while the leading chamber 9 is under pressure, i.e. inflated.

The automatic control system of the presently described embodiment includes a supply line 21 connecting a two-way valve or cock 22 via a line 23 to the second or trailing chamber 10, and a control unit of the two-way valve 22, including a diaphragm-type actuator 24 connected to the supply line 21 via a parallel arrangement of a pressure-controlled gate 25 and a check valve 26. The system further includes a pressure-limiting means in the connection between the supply line 21 and a line 27 feeding the internal space 17 of the bellows 13, including a parallel arrangement of a pressure-controlled gate 28 and a check valve 29. At its opposite end the internal scape 17 of the bellows 13 is connected via a line 30, a pressure-controlled gate 31 and a line 32 with the leading chamber 9. The lines 30 and 32 are connected to a pressure-relief line 33 including a diaphragm-type actuator 34 and a valve 35 controlling the connecting with the ambient atmosphere.

The internal space 17 of the bellows 13 accommodates an expansion-limiting means which in the presently described embodiment is in the form of a length of a cable 36 having its opposite ends secured in the centres of the respective bottoms 11 and 12 of the sleeves 5 and 6.

Pickups 37 for ultrasonic inspection of the pipeline 3 are accommodated in either one or both of the chambers 9 and 10 and secured to the respective sheaths 7 or 8.

Eddy-current pickups 38 are accommodated internally of either one or both of the sleeves 5 and 6.

The operating principle of the herein disclosed device is based on the alternating motion of the two support end assemblies 1 relative to each other, at least one of the two engaging the internal surface 2 of the pipeline 3. This relative motion of the support end assemblies 1 is effected by varying the length of the motion member 4, i.e. of the bellows 13. The required alternation of the pressure supply to the chambers of the support end assemblies and to the internal space of the bellows is effected by the automatic control system.

The device is operated, as follows. Compressed air is supplied from the pressure delivery connection 19 of the compressor 18 via the two-way valve 22 into the supply line 21. The two-way valve 22 is operated by the diaphragm-type actuators 24 to connect the supply line 21 automatically either to the pressure connection 19 of the compressor 18 or to the intake or suction connection 20 thereof. In the initial position of the operation the two-way valve 22 is set to connect the supply line 21 to the pressure delivery connection 19.

From the supply line 21 compressed air flows via the line 23 into the trailing chamber 10, inflating the latter and making the inflated elastic sheath 8 firmly engage the internal surface 2 of the pipeline 3. At this stage the supply of compressed air into the diaphragm-type actuator 24 is cut off by the closed pressure-controlled gate 25 and the check valve 26, while the supply of compressed air into the internal space 17 of the bellows 13 via the line 27 is cut off by the closed pressure-controlled gate 28 and the check valve 29.

Figure 3:
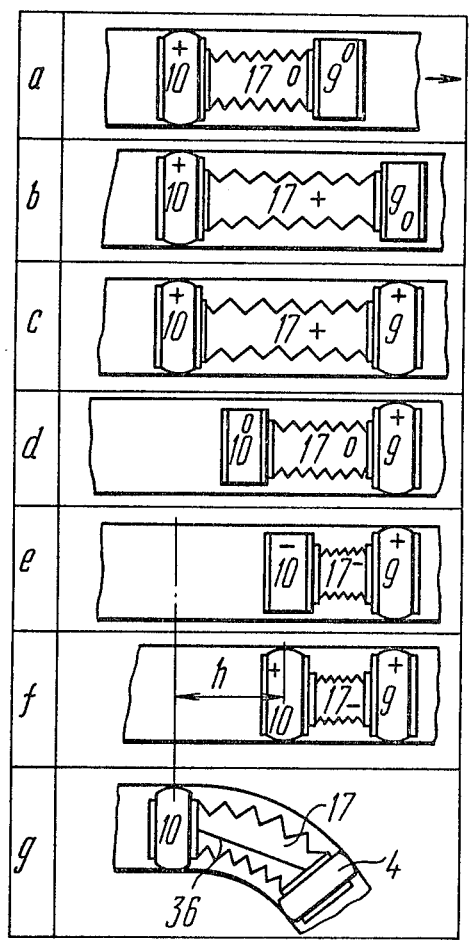
FIG. 3 shows schematically the successive positions of the components of the device during a single stepping cycle in which pressure in the internal spaces of chambers and bellow is denoted as follows: positive (higher atmospheric)—by sign (+), negative (lower atmospheric)—by sign (−), atmospheric—by sign (o).

The pressure-controlled gates 25, 28 and 31 are preadjusted to open automatically at pressure values $P_1$, $P_2$ and $P_3$, respectively, so that $P_1 > P_2 > P_3$. Therefore, compressed air flows from the supply line 21 via the line 23 into the trailing chamber 10, until the pressure therein is built up to the value $P_2$ which is the pressure value opening the gate 28. This completes the stage of retaining the trailing support end assembly 1 in the pipeline 3, as it is shown in FIG. 3a. Now compressed air flows via the now-opened gate 28 and the line 27 into the internal space 17 of the bellows 13. Meanwhile, the supply of compressed air into the leading chamber 9 is cut-off by the closed gate 31. As the pressure is built up in the internal space 17 of the bellows 13, the latter expands axially of the pipeline 3, in which way the sleeve 5 with the chamber 9 is displaced relative to the retained sleeve 6 with the chamber 10. Radial expansion of the bellows 13 is prevented by the incorporation of the rigid rings 15 and 16. The bellows 13 expands axially to the length permitted by the expansion-limiting cable 36. The completes the stage of moving the leading sleeve 5 with the chamber 9 relative to the trailing sleeve 6 with the chamber 10, as it is shown in FIG. 3b.

The continuing supply of compressed air into the internal space 17 of the bellows 13 builds up the pressure therein and in the line 30 to the value $P_3$, whereby the gate 31 automatically opens, and compressed air flows into the leading chamber 9 via this gate 31 and the line 32. The pressure-relief line 33 is meanwhile closed by the atmosphere connection-controlling valve 35 operated by the diaphragm-type actuator 34. The diaphragm-type actuator 34 being so constructed that it connects the line 33 with the ambient atmosphere via the valve 35 only while the pressure in the line 30 changes from negative to positive, i.e. from suction to gauge pressure, the continuing supply of compressed air into the chamber 9 builds up the pressure therein, inflating the chamber and urging the sheath 7 into film engagement with the internal space 2 of the pipeline 3, as it is shown in FIG. 3c.

In this position shown in FIG. 3c the further expansion of the bellows 13 is made impossible by the taut cable 36, and both support end assemblies 1 have their respective chambers 9 and 10 inflated into engagement with the surface 2 of the pipeline 3, whereby the pressure in the supply line 21, in the internal space 17 of the bellows 13 and in the chambers 9 and 10 is built up still further. As it becomes equal to the value $P_1$, the control gate 25 opens, and compressed air is fed into the diaphragm-type actuator 24 which operates the two-way valve 22.

With the two-way valve 22 thus switched over, the intake or suction connection 20 becomes connected to the supply line 21, whereby there begins evacuation of air from the trailing chamber 10, from the internal space 17 of the bellows 13 via the check valve 29 and from the diaphragm-type actuator 24 via the check valve 26.

The leading chamber 9 remains under gauge pressure, since it is cut off from the line 30 by the gate 31, while the diaphragm-type actuator 34 would not operate when the pressure in the line 30 is reduced from positive to negative. This position is shown in FIG. 3d.

As compressed air is evacuated from the internal space 17 of the bellows 13, the latter contracts, whereby the sleeve 6 with the chamber 10 is moved toward the sleeve 5 with the chamber 9 engaging the internal surface 2 of the pipeline 3.

Meanwhile, the pressure in the diaphragm-type actuator 24 is being reduced still further, but the latter is yet incapable of switching over the two-way valve 22, since it is adjusted to perform the switching-over when the suction attains the value $P_4$ at which the bellows 13 is completely contracted, as it is shown in FIG. 3e.

The compressor now operates solely to reduce the pressure in the entire system except the chamber 9 which is still under the pressure $P_1$.

Upon the suction having attained the value $P_4$, the diaphragm-type actuator 24 operates to switch over the two-way valve 22, so that the latter connects the supply line 21 once again to the pressure delivery connection 19 of the compressor 18.

Compressed air now flows once again from the supply line 21 via the line 23 to the chamber 10, whereby the latter's elastic sheath 8 is inflated into firm engagement with the internal surface 2 of the pipeline 3, as it is shown in FIG. 3f.

The diaphragm-type actuator 24 and the internal space 17 of the bellows 13 are cut off from the supply line 21, as it has been already described hereinabove. Upon the pressure in the chamber 10 having been built up the value $P_2$, the control gate 28 opens, and compressed air flows into the internal space 17 of the bellows 13 and into the line 30. As the compressed air feed is continued, the pressure in the line 30 changes from negative to positive, i.e. from suction to gauge pressure, whereby the actuator 34 operates, and the chamber 9 is connected for a brief instant to the ambient atmosphere via the atmosphere valve 35. Then the atmosphere valve 35 closes, and the pressure in the chamber 9 becomes equal to the atmospheric one, i.e. to the zero gauge pressure. In this way the device acquires the position illustrated in FIG. 3a.

The device has thus been driven through a complete stepping cycle and has covered the distance "h" shown in FIG. 3f.

When the device passes through curving portions of the pipeline, as it is shown in FIG. 3g, the bellows 13 expands as the pressure is built up in its internal space 17, while the cable 36 is offset from the axis of the bellows 13 and facilitates the curving of the path of the device, retaining at each portion of the path the position occupied by the bellows 13, whereby there appears a component of the effort applied to the bottom 11 of the sleeve 5 and urging the lateral toward the centre of the curvature.

To conduct the inspection of the properties of the material of the pipeline with aid of the pickups 37, 38, it is necessary, upon the device having arrived at the requested spot, to disconnect the compressor 18 from the supply line 21 with the device being in the position illustrated in FIG. 3c.

The travel abilities of the herein disclosed device enable to use to carry flaw-detecting pickups into the inspection area through pipelines having practically any three-dimensional pattern, including curvilinear portions with small curvature radii, as well as portions with somewhat oval shape and irregular internal surface. The presence of smaller-diameter tap lines leading from the main pipeline would not affect the travel ability of the herein disclosed device, either.

The disclosed automatic control system is simple both in structure and in adjustment and reliable in operation.

The presence of a single supply line increases the operating range of the device and its payload, while bringing down the failure probability.

What is claimed is:

1. A device for stepwise successively advancing flaw detection pickups through a pipeline, including: a compressor; a pressure delivery connection of said compressor; a selectively connected intake of said compressor; two support end assemblies for supporting said flaw detection pickups and being adapted to alternatingly engage the internal surface of the pipeline, each said support end assembly having a cup-shaped sleeve with a lateral surface and a bottom, and an elastic sheath accommodated on said lateral surface of said sleeve and defining therewith an annular chamber; a motion member having its length variable upon either one of said support end assemblies having engaged the surface of the pipeline, said motion member interconnecting said two support end assemblies and including a bellows secured between the respective said bottoms of said two sleeves: an automatic control system; said chambers and said bellows communicating with said compressor through a fluid line and said automatic control system includes value means so arranged that at the initial stage of each successive advancing step a leading one of said two chambers is connected to the ambient atmosphere, while a trailing one of said two chambers and said bellows are connected to said pressure delivery connection of said compressor, whereas at the end of the step said trailing chamber and said bellows are connected to said intake connection of said compressor, while said leading chamber is under pressure.

2. A device as set forth in claim 1, wherein said bellows includes an array of frustoconical elastic elements having its opposite ends secured to respective rigid rings adjoining the corresponding rings of the adjacent elements.

3. A device as set forth in claim 1, wherein said automatic control system includes a supply line connecting a two-way valve with said trailing chamber, the control unit of said two-way valve including a diaphragm-type actuator operatively connected with said two-way valve and communicating with said supply line through a parallel arrangement of a pressure-controlled gate and a check valve; a pressure-limiting means connecting said supply line with the internal space of said bellows and comprising another pressure-controlled gate and another check valve arranged parallel with each other; a third pressure-controlled gate connecting the internal space of said bellows with said leading chamber; and a pressure-relief line including another diaphragm-type actuator and a valve controlling the communication with the ambient atmosphere, said pressure-relief line being also connected with said leading chamber.

4. A device as set forth in claim 1, wherein the internal space of said bellows accommodates an expansion-limiting means.

5. A device as set forth in claim 4, wherein said expansion-limiting means includes a length of a cable having its ends secured in the centres of the respective bottoms of said cup-shaped sleeves.

6. A device as set forth in claim 1, wherein the internal space of at least one of said chambers has pickups for acoustic inspection of the pipeline secured therein to said respective sheath.

7. A device as set forth in claim 1, wherein the internal space of at least one of said two- cup-shaped sleeves accommodates therein eddy-current pickups.

* * * * *